United States Patent [19]

Newman-Evans

[11] Patent Number: 4,814,414

[45] Date of Patent: Mar. 21, 1989

[54] EPOXY RESINS BASED ON TETRAGLYCIDYL DIAMINES

[75] Inventor: Richard H. Newman-Evans, Somerville, N.J.

[73] Assignee: Amoco Corporation, Chicago, Ill.

[21] Appl. No.: 134,242

[22] Filed: Dec. 17, 1987

Related U.S. Application Data

[60] Continuation of Ser. No. 22,653, Mar. 6, 1987, abandoned, which is a division of Ser. No. 853,052, Apr. 17, 1986, Pat. No. 4,680,341.

[51] Int. Cl.$^4$ .............................................. C08G 59/32
[52] U.S. Cl. .................................... 428/273; 428/272; 428/290; 525/484; 528/103; 528/361; 528/407; 528/99; 528/229; 528/373; 523/222; 523/428; 523/433; 523/434; 523/445; 523/457; 523/466; 523/468
[58] Field of Search ............... 523/222, 428, 433, 434, 523/445, 457, 466, 468; 428/272, 273, 413, 415, 290; 528/99, 103, 229, 373, 361, 407; 525/484

[56] References Cited

U.S. PATENT DOCUMENTS

| | | | |
|---|---|---|---|
| 2,951,822 | 9/1960 | Reinking | 528/418 X |
| 4,451,645 | 5/1984 | Johncock | 528/407 X |
| 4,487,948 | 12/1984 | Shimp et al. | 528/418 X |
| 4,510,272 | 4/1985 | Loszewski | 523/400 |
| 4,656,207 | 4/1987 | Jabloner et al. | 523/400 |

OTHER PUBLICATIONS

Shell Chemical Co. Development Product Tech. Bulletin No. SC:875-86, "EPON HPT Resin 1071", Mar. 1986.
May and Tanaka, "Epoxy Resins", Marcel Dekker, New York 1973, pp. 601-602, TP1180.E6.E66.

Primary Examiner—Earl Nielsen
Attorney, Agent, or Firm—Richard J. Schlott; William H. Magidson; Ralph C. Medhurst

[57] ABSTRACT

Novel 3-ring tetraglycidates having the formula

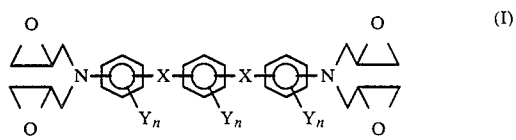

(I)

wherein

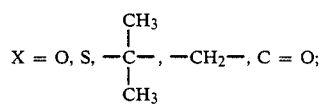

Y = halogen, $C_1$-$C_4$ alkyl; and
n = 0 to 4, are disclosed.

Epoxy resin systems exhibiting good tensile properties and moisture sensitivity can be made by copolymerizing the tetraglycidates with a polyamine curing agent. Prepregs can be made by combining the epoxy resin systems with a fiber reinforcement. The epoxy resin system may include a co-epoxide.

34 Claims, No Drawings

EPOXY RESINS BASED ON TETRAGLYCIDYL DIAMINES

This is a continuation of application Ser. No. 022,653, filed 3/6/87, abandoned which is a divisional of Ser. No. 853,052, filed 04/17/86 now U.S. Pat. No. 4,680,341.

FIELD OF THE INVENTION

This invention relates to novel 3-ring tetraglycidates, to epoxy resin systems made from the novel tetraglycidates, to prepregs made using the epoxy resin systems, and to articles of manufacture which incorporate the epoxy resins or the prepregs.

BACKGROUND OF THE INVENTION

Polyglycidates (also referred to herein as epoxy compounds) generally constitute a class of compounds having at least two glycidyl groups, the reactive moiety in each glycidyl group being the epoxy group.

Many epoxy compounds are commercially available for use in epoxy resin systems including 2-ring structures such as N,N,N',N',-tetraglycidyl-4,4'-methylene dianiline, having the structure

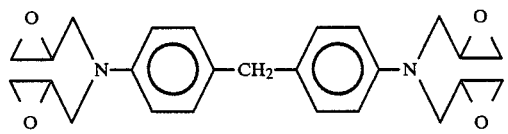

This material is made by reacting an excess of epichlorohydrin with methylene dianiline. It is available commercially as MY-720 from Ciba Geigy Corp., Ardsley, N.Y. and consists of about 70% by weight of the above tetraglycidate, the remainder being oligomers and triglycidates.

Another commonly used 2-ring epoxy compound is made by reacting bisphenol A with epichlorohydrin. Commercially available resins made from this reaction contain the structure

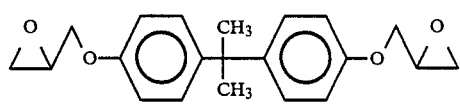

and include DER 331 from Dow Chemical and EPON® 828 (registered trademark) from Shell.

Epoxy groups are reactive to amine and hydroxyl functionalities and can thus be copolymerized (i.e. cured) with compounds containing such functionalities to make epoxy resin systems. Generally polyamines are favored as curing agents although polyhydroxy curing agents are also well known. The epoxy compounds can be reacted with one or more curing agents such that they are crosslinked, thereby finding use as structural adhesives or as encapsulating materials for electronic components.

Epoxy resin systems are often used in prepregs, ready-to-mold materials comprising fibrous reinforcement impregnated with uncured or partially cured epoxy resin systems. Prepregs can be assembled into a final part (such as an airplane wing) and fully cured (C-staged) to form a finished product. Such prepregs find wide use in the aircraft and aerospace industries.

Key properties of epoxy resin systems are tensile properties and moisture sensitivity. High tensile strength is desirable in, for example, structural adhesives. Low moisture sensitivity is also desirable since it leads to improved performance under hot/wet conditions.

Most advanced composites are fabricated from prepreg. Resin systems containing an epoxy compound such as MY-720 and aromatic amine hardener are often used in prepreg since they possess the balance of properties required for this material. State-of-the-art epoxy/carbon fiber composites have high compressive strengths, good fatigue characteristics, and low shrinkage during cure. However, since most epoxy formulations used in prepreg are brittle, these composites have poor impact resistance. In addition, epoxy formulations absorb moisture which reduces their high temperature properties and affects their dimensional stability.

Thus, new epoxy compounds which could be used to make epoxy resin systems which improve such desirable physical and mechanical properties, relative to present state-of-the-art epoxy systems, would be a useful addition to the structural adhesive, airplane, aerospace, and other like art areas.

THE INVENTION

The present invention provides, in one aspect, novel tetraglycidates of the formula

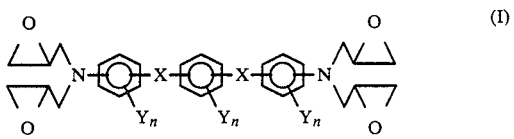

wherein

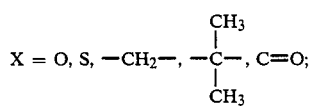

Y = halogen, $C_1$–$C_4$ alkyl; and
n = 0 to 4.

Preferred tetraglycidates of the present invention include:

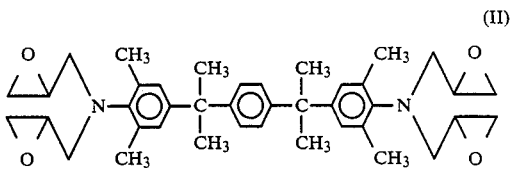

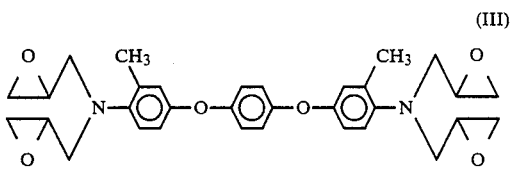

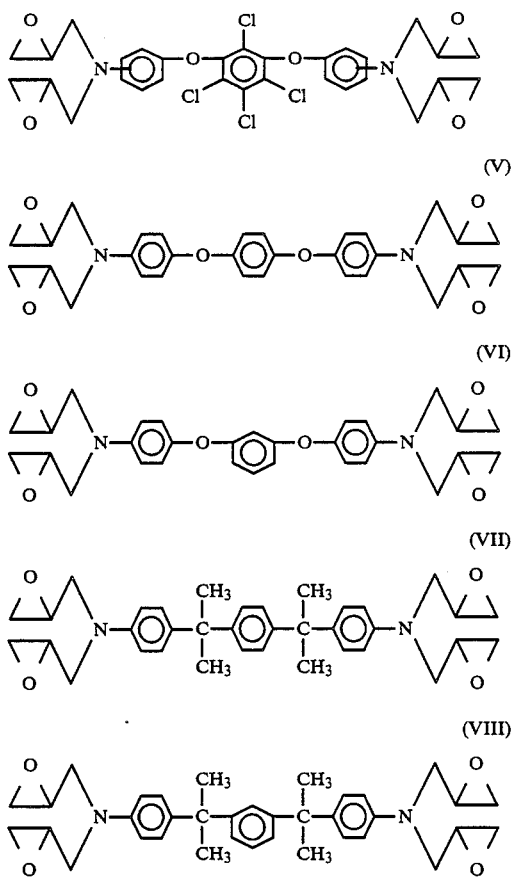

In another aspect, the invention provides novel epoxy resin systems comprising a tetraglycidate having the above formula (I) copolymerized with a polyamine curing agent (also referred to herein as a hardener). The polyamine hardener may, for example, be any of the well known aliphatic polyamines such as diethylene triamine, triethylene tetraamine, or tetraethylene pentaamine. Additional hardeners are those containing benzenoid unsaturation such as m- and p-phenylenediamine, 1,6-diaminonaphthalene, 4,4'-diaminodiphenyl methane (also known as 4,4'-methylene dianiline), 4,4'-diaminodiphenyl ether, sulfanilamide, 3methyl-4-aminobenzamide, and 4,4'-diaminodiphenyl sulfone (DDS), 4,4'-diaminodiphenyl, ring-alkylated derivatives of m-phenylene diamine such as ETHACURE ® 100 from Ethyl Corp., Baton Rouge, LA, and the like. Another useful class of polyamine curing agents are those disclosed in U.S. Pat. No. 4,521,583, which have the formula

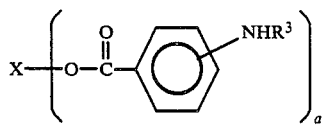

wherein a is 2 or 3, $R^3$ is hydrogen, alkyl of 1 to 8 carbon atoms or aryl of 6 to 18 carbon atoms, and X is a divalent or trivalent organic hydrocarbon, hetero-interrupted hydrocarbon, or substituted hydrocarbon radical or

These hardening agents may be prepared from corresponding starting materials, e.g., nitro compounds, by reduction, for example, according to methods described in U.K. Pat. No. 1,182,377. Particularly contemplated are those compounds (IX) wherein $R^3$ is hydrogen or $C_1$-$C_3$ alkyl and X is a divalent or trivalent radical selected from (1) divalent groups consisting of —$(CH_2)_y$— wherein y is an integer of from 2 to 12,

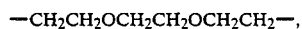

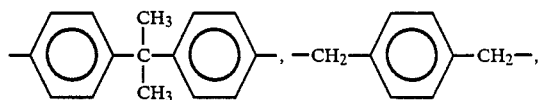

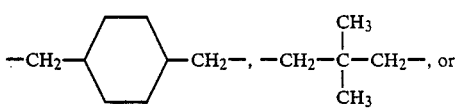

(2) trivalent groups of the formula

wherein n and m are the same or different integers from 1 to 4.

Preferred curing agents are (i) DDS, (ii) those diamines having the formula

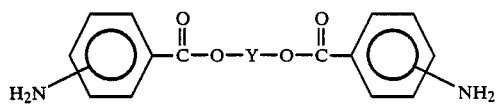

wherein each of the two amino groups is meta or para to the carbonyl group bonded to the same ring and wherein Y is

wherein q is an integer from 2 to 12, preferably 2 to 6, and most preferably 3;

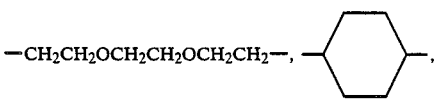

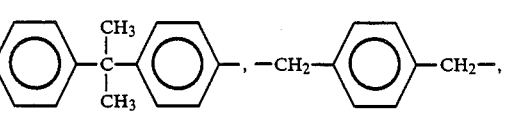

-continued

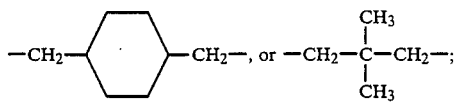

(iii)
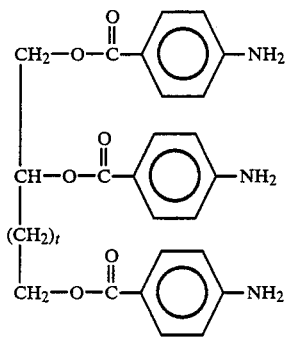

wherein t is an integer of from 0 to about 5; and (iv)
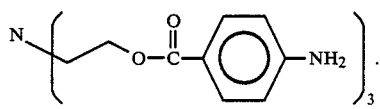

The polyamine curing agent and epoxy compound are mixed essentially in an amount which provides about 0.3 to about 2.0, preferably about 0.4 to 1.7, and most preferably about 0.45 to about 1.3 moles of amine hydrogen for each mole of epoxy groups. The epoxy resin system comprising the curing agent and epoxy compound may be cured by heating between about 200°–400° F. for time periods ranging between about 0.5 and about 12 hours.

In another aspect, this invention provides prepregs comprising the novel epoxy resins described herein. Prepregs contain structural fibers. The structural fibers which are useful in this invention include carbon, graphite, glass, silicon carbide, poly(benzothiazole), poly(benzimidazole), poly(benzoxazole), alumina, titania, boron, and aromatic polyamide fibers. These fibers are characterized by a tensile strength of greater than 100,000 psi, a tensile modulus of greater than two million psi, and a decomposition temperature of greater than 200° C. The fibers may be used in the form of continuous tows (500 to 400,000 filaments each), woven cloth, whiskers, chopped fiber or random mat. The preferred fibers are carbon and graphite fibers, aromatic polyamide fibers, such as Kevlar 49 fiber (obtained from E. I. duPont de Nemours, Inc., Wilmington, DE), and silicon carbide fibers.

The epoxy resin in this invention is prepared by standard methods, such as that described in U.S. Pat. No. 2,951,822 and also in an article by W. T. Hodges et al., SAMPE Quarterly, October 1985, pages 21–25, both of which are incorporated herein by reference. The method entails reacting an aromatic diamine with a four to twenty molar excess of epichlorohydrin at elevated temperature, generally 50° to 100° C. This is followed by dehydrochlorination of the intermediate chlorohydrin amine with aqueous base. The product is then isolated by diluting with a water immiscible solvent, washing with water, drying with a suitable desiccant, and concentrating to obtain a resinous product. The epoxide thus obtained generally is found by titration to contain 70 to 90% of the theoretical amount of epoxy groups. This is due to formation of oligomeric residues and/or incomplete reaction of the monomeric diamine with epichlorohydrin. For example, Kirk-Othmer Encyclopedia of Chemical Technology, 3rd edition, Volume 9, page 277, gives the epoxy equivalent weight (EEW) of MY-720 (a commonly used commercial glycidyl amine) as 117–133. The theoretical EEW is 105. The materials are further characterized by liquid chromatography, infrared spectroscopy, and nuclear magnetic resonance.

The diamines used to form the tetraglycidates of this invention may be prepared by one or more methods disclosed in the literature. For example, one general route for preparing the diamines involves the reaction of alpha,alpha'dihydroxy-para-diisopropylbenzene with aniline in the presence of an acidic alumina catalyst and heating the mixture to 160°–220° C. to give alpha,alpha'-bis(4-aminophenyl)-para-diisopropylbenzene. Details of the method are reported by H. J. Buysch et al. in German Offen. DE No. 2,111,194 published Sept. 14, 1972. A similar method is also disclosed for the preparation of substituted aminoaryl compounds and derivatives in Netherlands patent application No. 6,408,539 of Jan. 20, 1965 by Allied Chemical Corp.

Another general method which can also be employed for the preparation of the diamine starting materials involves the reaction of a diisopropenylbenzene with an aniline hydrochloride under a nitrogen atmosphere and at temperatures of from 180°–200° C. as disclosed in U.S. Pat. No. 3,206,152 assigned to Farbenfabriken Bayer, A.G. A further method for preparing the diamines starting from diisopropenylbenzene is disclosed in U.S. Pat. No. 3,365,347 which issued Jan. 23, 1968 to Allied Chemical Corp.

Certain of the diamine hardeners are available commercially, such as for example, alpha,alpha'-bis(4-aminophenyl)-meta-diisopropylbenzene and alpha,alpha'-bis(4-aminophenyl)-para-diisopropylbenzene which can be obtained from Mitsui Petrochemicals Industries Ltd., Japan having an office at 200 Park Avenue, New York, N.Y. 10017. Additionally, the diamine hardeners 1,3-bis(4-aminophenyl)benzene and 1,3-bis(3-aminophenoxy)benzene are available from Wakayama Seika, Japan. The preparation of other aromatic diamines are described in U.S. Pat. No. 4,222,962 which issued Sept. 16, 1980 to J. P. Pellegrini, Jr.

Epoxy resin systems, i.e., epoxy resin plus hardener, are prepared by heating and stirring the epoxy resin to 60° to 120° C. and adding the hardener. If the hardener is a solid, it is preferably added as a fine powder. An inert diluent such as N,N-dimethyl formamide or N-methylpyrrolidone may be used if desired. Reaction of the epoxy and hardener occur as the mixture is heated. For prepreg, the mixture is B-staged or partially reacted (i.e. typically 3 to 15 percent of the epoxy groups are reacted) in order to obtain a resin system with the required physical properties (i.e. viscosity and tack).

Prepregs according to the present invention can be made by embedding filaments or fibers into, or by coating woven or non-woven webs, rovings, tows, or the like, with a curable epoxy resin resin matrix which is ultimately manipulated and cured to a solid composite. Particular selection of the filament, fiber, or textile material, epoxy compound, and curing agent can give a range of curable composites which can be tailored to suit a given need or application.

It is preferred to apply the resin as a hot melt to the fiber reinforcement. The B-staged epoxy resin system may conveniently first be applied to long sheets of differential release paper, i.e. paper to which a release agent such as any of several of the silicone formulations well known in the art, has been applied. In a prepreg machine, resin coated on the release paper is transferred to a web of fiber. This is done by sandwiching the web between plies of coated release paper and passing the material through a set of heated rollers. The resulting prepreg is then cooled and taken up on a spool. The total amount of resin applied to the fiber reinforcement is preferably between about 20 and about 50 wt. percent of resin solids based on the weight of the uncured composite. If desired, the prepreg may at this point be cooled to 0° F. or less by exposure to any convenient cryogenic material (such as dry ice) for shipping or storage.

Upon rewarming to about room temperature, the prepreg can then be used to make structural parts such as airplane wings or fuselage components. The prepreg may also be used to make other useful articles such as golf shafts, tennis rackets, musical instruments, satellite components, and rocket motors. To make useful articles from prepreg, the prepreg may be cut into strips and then laid up (e.g. on a mold surface) to create the desired shape. The shaped, layered composite is then fully cured at pressures between about atmospheric to about 500 psi and temperatures between about 100° C. to about 300° C. in an oven, autoclave, or heated pressure mold. Depending on the exact epoxy formulation, temperature, and pressure, curing times may range between about 0.2 and about 8 hours, the optimum time, pressure, and temperature being easily ascertainable by means of trial runs. This final cure essentially C-stages the composite, meaning that the resin has substantially reached the final stage of polymerization where cross-linking becomes general and the composite is substantially infusible.

When making the epoxy resin system for use generally or for use specifically as a prepreg, a modifying thermoplastic polymer, polymer blend, or elastomer may be used to adjust the viscosity of the resin and to desirably enhance processability and mechanical properties, particularly toughness and damage tolerance. The classes of resins which are broadly useful include poly(aryl ether) resins as disclosed, for example, in U.S. Pat. Nos. 4,175,175 and 4,108,837 and exemplified by thermoplastic poly(aryl ether sulfones) available commercially under the registered trademark UDEL ® from Union Carbide Corporation, polyetherimides available, for example, under the registered trademark ULTEM ® from General Electric, phenoxy resins (of the type commercially available under the registered trademark UCAR ® from Union Carbide Corporation), polyurethanes, butadiene/styrene/acrylonitrile terpolymers, nylons, butadiene/acrylonitrile liquid rubbers such as HYCAR ® CTBN from B. F. Goodrich and the like. The amount of thermoplastic resin employed will generally fall in a range of about 1 to about 30 wt.% based on the weight of the epoxy resin system, although amounts above or below this range may be desired in certain applications. Preferred thermoplastic resins include poly(aryl ether sulfones), polyetherimides, phenoxy resins, and butadiene/acrylonitrile liquid rubbers. The thermoplastic resin is generally added to the epoxy compound and mixed therewith prior to addition of the polyamine curing agent. The modifier will often be miscible with the epoxy compound, although it will also often be occluded as a dispersion within the final cured epoxy resin once the resin is thermoset.

Co-epoxides may also be used in the epoxy resin system. The co-epoxy compounds (or resins), when employed, may be present in an amount up to about 40 wt.%, preferably up to about 30 wt.%, based on the amount of (cured or uncured) tetraglycidate used.

Co-epoxy compounds which may be used herein contain two or more epoxy groups having the following formula:

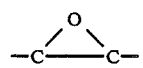

The epoxy groups can be terminal epoxy groups or internal epoxy groups. The epoxides are of two general types: polyglycidyl compounds or products derived from epoxidation of dienes or polyenes. Polyglycidyl compounds contain a plurality of 1,2-epoxide groups derived from the reaction of a polyfunctional active hydrogen containing compound with an excess of an epihalohydrin under basic conditions. When the active hydrogen compound is a polyhydric alcohol or phenol, the resulting epoxide composition contains glycidyl ether groups. A preferred group of polyglycidyl compounds are made via condensation reactions with 2,2-bis(4-hydroxyphenyl)propane, also known as bisphenol A, and have structures such as (X),

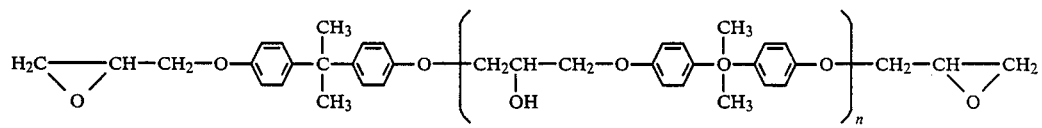

where n has a value from about 0 to about 15. These epoxides are bisphenol-A epoxy resins. They are available commercially under the trade names such as "Epon 828," "Epon 1001", and "Epon 1009" from Shell Chemical Co. and as "DER 331", "DER 332", and "DER 334" from Dow Chemical Co. The most preferred bisphenol A epoxy resins have an "n" value between 0 and 10.

Polyepoxides which are polyglycidyl ethers of 4,4'-dihydroxydiphenyl methane, 4,4'-dihydroxydiphenyl sulfone, 4,4'-biphenol, 4,4'-dihydroxydiphenyl sulfide, phenolphthalein, resorcinol, 4,2'-biphenol, or tris(4-hydroxyphenyl)methane and the like, are useful in this invention. In addition, EPON 1031 (a tetraglycidyl derivative of 1,1,2,2-tetrakis(hydroxyphenyl)ethane from Shell Chemical Company), and Apogen 101, (a methylolated bisphenol A resin from Schaefer Chemical Co.) may also be used. Halogenated polyglycidyl compounds such as D.E.R. 542 (a brominated bisphenol A epoxy resin from Dow Chemical Company) are also useful. Other suitable epoxy resins include polyepoxides prepared from polyols such as pentaerythritol, glycerol, butanediol or trimethylolpropane and an epihalohydrin.

Polyglycidyl derivatives of phenol-formaldehyde novolaks such as XI where n=0.1 to 8 and cresol-formaldehyde novalaks such as XII where n=0.1 to 8 are also useable.

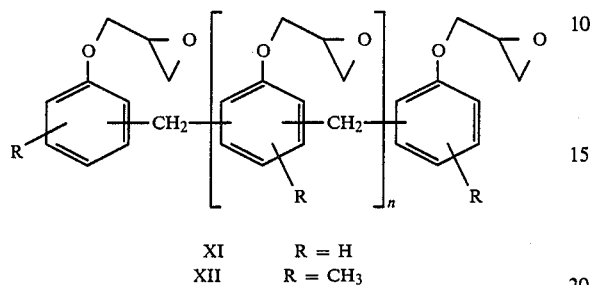

XI  R = H
XII R = CH₃

The former are commercially available as D.E.N. 431, D.E.N. 438, and D.E.N. 485 from Dow Chemical Company. The latter are available as, for example, ECN 1235, ECN 1273, and ECN 1299 (obtained from Ciba-Geigy Corporation, Ardsley, NY). Epoxidized novolaks made from bisphenol A and formaldehyde such as SU-8 (obtained from Celanese Polymer Specialties Company, Louisville, KY) are also suitable.

Other polyfunctional active hydrogen compounds besides phenols and alcohols may be used to prepare the polyglycidyl adducts useful in this invention. They include amines, aminoalcohols and polycarboxylic acids.

Adducts derived from amines include N,N-diglycidyl aniline, N,N-diglycidyl toluidine, N,N,N',N'-tetraglycidyl xylylenediamine, (i.e., XIII) N,N,N',N'-tetraglycidyl-bis(methylamino)cyclohexane (i.e. XIV), N,N,N',N'-tetraglycidyl-4,4'-methylene dianiline, (i.e. XV) N,N,N,',N'-tetraglycidyl-3,3'-diaminodiphenyl sulfone, and N,N'-dimethyl-N,N'-diglycidyl-4,4'-diaminodiphenyl methane. Commercially available resins of this type include Glyamine 135 and Glyamine 125 (obtained from F.I.C. Corporation, San Francisco, CA.), Araldite MY-720 (obtained from Ciba Geigy Corporation) and PGA-X and PGA-C (obtained from The Sherwin-Williams Co., Chicago, Ill.).

Also suitable are modified epoxies such as Tactix 71788, 71794, and 71795 epoxy resins (obtained from Dow Chemical Corporation, Midland, MI.).

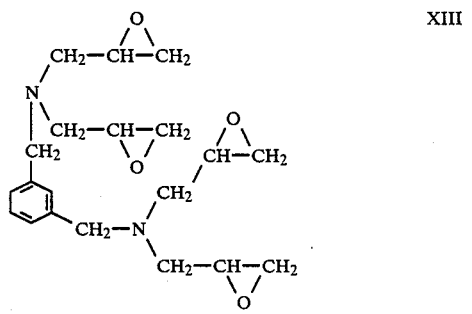

XIII

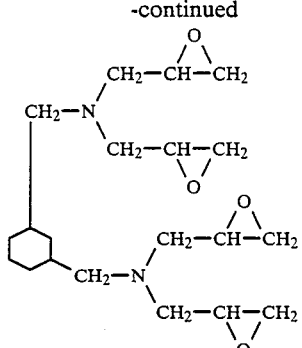

XIV

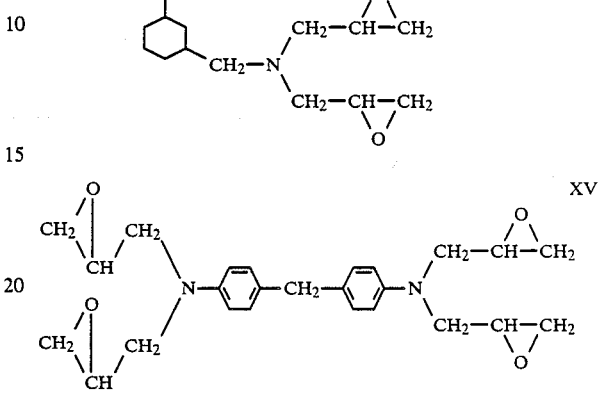

XV

Suitable polyglycidyl adducts derived from aminoalcohols include O,N,N-triglycidyl-4-aminophenol, available as Araldite 0500 or Araldite 0510 (obtained from Ciba Geigy Corporation) and O,N,N-triglycidyl-3-aminophenol (available as Glyamine 115 from F.I.C. Corporation).

Also suitable for use herein are the glycidyl esters of carboxylic acids. Such glycidyl esters include, for example, diglycidyl phthalate, diglycidyl terephthalate, diglycidyl isophthalate, and diglycidyl adipate. There may also be used polyepoxides such as triglycidyl cyanurates and isocyanurates, N,N-diglycidyl oxamides, N,N'-diglycidyl derivatives of hydantoins such as "XB 2793" (obtained from Ciba Geigy Corporation), diglycidyl esters of cycloaliphatic dicarboxylic acids, and polyglycidyl thioethers of polythiols.

Other epoxy-containing materials are copolymers of acrylic acid esters of glycidol such as glycidyl acrylate and glycidyl methacrylate with one or more copolymerizable vinyl compounds. Examples of such copolymers are 1:1 styrene-glycidyl methacrylate, 1:1 methyl methacrylate-glycidyl acrylate and 62.5:24:13.5 methyl methacrylate:ethyl acrylate:glycidyl methacrylate.

Silicone resins containing epoxy functionality, e.g., 2,4,6,8,10-pentakis[3-(2,3-epoxypropoxy)propyl]-2,4,6,8,10-pentamethylcyclopentasiloxane and the diglycidyl ether of 1,3-bis-(3-hydroxypropyl)tetramethyldisiloxane) are also useable.

The second group of epoxy resins is prepared by epoxidation of dienes or polyenes. Resins of this type include bis(2,3-epoxycyclopentyl)ether, XVI,

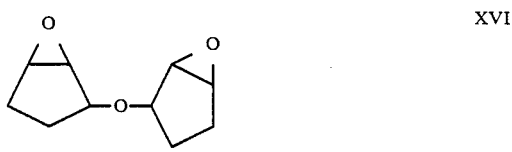

XVI

-continued

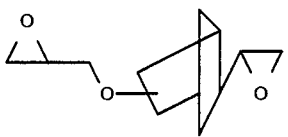

XVII

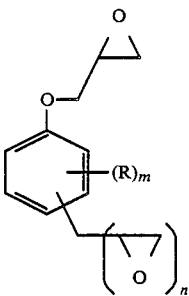

copolymers of XVI with ethylene glycol which are described in U.S. Pat. No. 3,398,102, 5(6)-glycidyl-2-(1,2-epoxyethyl)bicyclo[2.2.1]heptane, XVII, and dicyclopentadiene diepoxide. Commercial examples of these epoxides include vinylcyclohexene dioxide, e.g., "ERL-4206" (obtained from Union Carbide Corp.), 3,4-epoxycyclohexylmethyl 3,4-epoxycyclohexane carboxylate, e.g., "ERL-4221" (obtained from Union Carbide Corp.), 3,4-epoxy-6-methylcyclohexylmethyl 3,4-epoxy-6-methylcyclohexane carboxylate, e.g., "ERL-4201" (obtained from Union Carbide Corp.), bis(3,4-epoxy-6-methylcyclohexylmethyl)adipate, e.g., "ERL-4289" (obtained from Union Carbide Corp.), dipentene dioxide, e.g., "ERL-4269"(obtained from Union Carbide Corp.) 2-(3,4-epoxycyclohexyl-5,5-spiro-3,4-epoxy)cyclohexanemetadioxane, e.g., "ERL-4234" (obtained from Union Carbide Corp.) and epoxidized polybutadiene, e.g., "Oxiron 2001" (obtained from FMC Corp.)

Other suitable cycloaliphatic epoxides include those described in U.S. Pat. Nos. 2,750,395; 2,890,194; and 3,318,822 which are incorporated herein by reference, and the following:

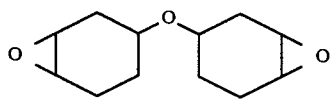

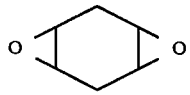

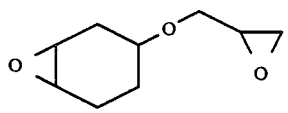

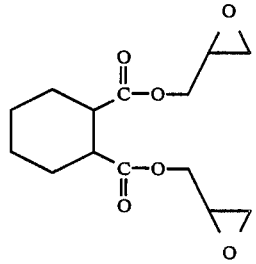

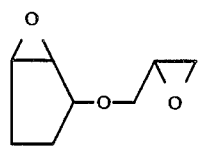

Other suitable epoxides include:

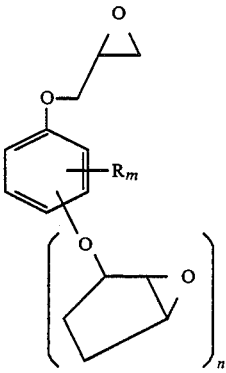

where n is 1 to 4, m is (5−n), and R is H, halogen, or $C_1$ to $C_4$ alkyl.

Reactive diluents containing one epoxide group such as t-butylphenyl glycidyl ether, may also be used. The reactive diluent may comprise up to 25 percent by weight of the epoxide component.

The preferred co-epoxy resins are bisphenol A epoxy resins of formula X where n is between 0 and 5, epoxidized novolak resins of formula XI and XII where n is between 0 and 3, N,N,N',N'-tetraglycidyl xylylene diamine, and diglycidyl phthalate.

The epoxy resin system may additionally contain an accelerator to increase the rate of cure. Accelerators which may be used herein include Lewis acid:amine complexes such as $BF_3$.monoethylamine, $BF_3$ piperidiene, $BF_3$.2-methylimidazole; amines, such as imidazole and its derivatives such as 4-ethyl-2-methylimidazole, 1-methylimidazole, 2-methylimidazole; N,N-dimethylbenzylamine; acid salts of tertiary amines, such as the p-toluenesulfonic acid:imidazole complex, salts of trifluoromethane sulfonic acid, such as FC-520 (obtained from 3M Company), organophosphonium halides, dicyandiamide, 1,1-dimethyl-3-phenyl urea (Fikure 62U from Fike Chemical Co.), and chlorinated derivatives of 1,1-dimethyl-3-phenyl urea (monuron and diuron from du Pont). If used, the amount of cure accelerator may be from 0.02 to 10 percent of the weight of the epoxy resin system (i.e., epoxy plus hardener).

In addition to structural fibers, thermoplastic polymers, and cure accelerators, the epoxy resin systems may also contain particulate fillers such as talc, mica, calcium carbonate, aluminum trihydrate, glass microballoons, phenolic thermospheres, pigments, dyes, and carbon black. In prepregs, up to half of the weight of structural fiber in the composition may be replaced by filler. Thixotropic agents such as fumed silica may also be used.

In the epoxy resin systems (i.e. epoxy plus hardener) of this invention, the proportion of epoxy resin can be about 95 to about 30 percent by weight, preferably about 80 to about 35 wt. percent, and the proportion of hardener can be from about 5 to about 70 wt. percent, preferably about 15 to about 60 wt. percent.

In prepregs and composites (epoxy plus hardener and structural fiber), the percent by weight of the epoxy resin system can be from about 20 to 80 percent by weight, based on the weight of the prepreg or composite, preferably about 25 to about 60 wt. percent. The structural fiber comprises 80 to 20 wt. percent, preferably 75 to 40 wt. percent of the total composition.

The invention is further disclosed and described by means of the following examples which are not to be taken as limiting.

EXAMPLE 1

This example describes the synthesis of Bisaniline P tetraglycidate (BAP TG) from Bisaniline P (BAP).

BAP (1.2 kg), epichlorohydrin (3.0 kg) ethanol (1.6 l), and 200 ml of water were placed into a 5 liter three neck, roundbottom flask that was equipped with a mechanical stirrer, addition funnel, and a thermometer that was connected to a Therm-o-watch temperature controller. The mixture was placed under a blanket of nitrogen and heated to reflux with gentle stirring. The reaction mixture was a slurry initially but quickly became homogeneous as the reflux temperature was approached. After the mixture had refluxed for 4 hours, the temperature was lowered to 60° C. and 1.2 kg of 50% aqueous sodium hydroxide were added at such a rate that the temperature was maintained at 60° C. When addition was complete, the temperature was held at 60° C. for 1 hour, at which time heating was discontinued. When the mixture was at room temperature, the liquid was decanted from the flask into a separatory funnel. The large mass of sodium chloride left behind was washed with methylene chloride (2×100 ml) and these washings were added to the separatory funnel. Water (200 ml) was added to the separatory funnel and the layers were separated. The organic phase was washed with water (2×1 liter), brine (1×1 liter), dried (Na₂SO₄), filtered, and the filtrate was concentrated on a rotary evaporator (50 mm Hg, at 80° C., then 0.1 mm Hg at 80° C.). 1.9 kg (93%) of a light brown viscous liquid was obtained. Physical Data: Epoxy equivalent weight=160 g/eq.

EXAMPLE 2

This example describes the preparation of bis-1,4-(4-aminophenoxy)benzene tetraglycidate (TPE-QTG) from bis-1,4-(4-aminophenoxy)benzene (TPE-Q).

Following the procedure of Example 1, 200 g TPE-Q, 465 g epichlorohydrin, 200 ml ethanol, and 30 ml of water produced 310 g (70%) of a viscous liquid having an EEW=170 g/eq.

EXAMPLE 3

This example describes the preparation of 1,3-bis(4-aminophenoxy)benzene tetraglycidate (TPE-RTG) from 1,3-bis(4-aminophenoxy)benzene (TPE-R).

Following the procedure of Example 1, 1.0 kg TPE-R, 3.0 kg epichlorohydrin, 0.6 l ethanol, and 100 ml of water afforded 1.4 kg (82%) of a viscous amber liquid. EEW=174 g/eq.

The following examples describe the preparation of unreinforced castings of the new tetraglycidates cured with trimethylene glycol di-p-aminobenzoate (DADE).

Glass transition temperatures were determined on a DuPont 982 thermal analyzer as the maximum of the loss modulus peak of a DMA scan. Water sensitivity was determined by soaking a 2.0"×0.5"×⅛" coupon in water for 2 weeks at 71.1° C. (160° F.). The percent weight gain of the coupon was determined after soak.

EXAMPLE 4

40 g of the epoxy of Example 1 were heated to 100° C. in a three-neck 500 ml roundbottom flask fitted with a thermometer connected to a Therm-o-watch temperature controller and a mechanical stirrer. 24.0 g of DADE were added. After the temperature came back to 100° C., all the diamine dissolved after another 15–45 minutes. Vacuum (50 mm Hg) was applied for about 5 minutes, stirring was discontinued and the vacuum was applied for 5 minutes more. The resin was then poured into a mold (dimensions 8"×10"×⅛") which had been warmed in a 90° C. oven. The casting was cured as follows: 75° C. (4 hours)→4 hours→120° C. (2 hours)→2 hours→179° C. (2 hours).

EXAMPLE 5

Following the procedure of Example 4, 75 g of TPE-QTG and 45 g of DADE produced a void free, transparent casting.

EXAMPLE 6

Following the procedure of Example 4, 100 g TPE-RTG and 56 g of DADE produced a void free transparent casting.

Control A

This example is comparative and describes the preparation of unreinforced castings from an epoxy resin having the trade designation MY-720 and having as its major constituent a compound of the formula:

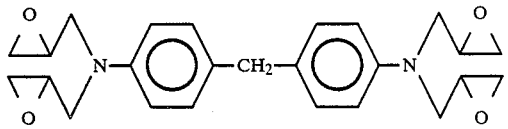

100 g of MY-720 were placed in a three-neck roundbottom flask equipped with a mechanical stirrer, thermometer fitted with a Therm-o-watch temperature controller, and a gas adaptor. The epoxy was warmed to 110° C., at which time 61 g of DADE were added. Heating was continued until the DADE was completely dissolved. Vacuum (50 mm Hg) was applied, and after 5 minutes stirring was stopped, the heating mantle was removed, and the vacuum was continued 5 more minutes. The resin was poured into a 8"×10"×⅛" mold that was prewarmed in a 100° C. oven.

Table I lists physical data for the castings of Examples 5–8 and Control A.

TABLE I

| | PROPERTIES OF UNREINFORCED CASTINGS | | | |
|---|---|---|---|---|
| | Example 4 | Example 5 | Example 6 | Control A |
| Composition[a] | BAPTG 40 g | TPE-QTG 75 g | TPE-RTG 100 g | MY-720 100 g |

TABLE I-continued

| PROPERTIES OF UNREINFORCED CASTINGS | | | | |
|---|---|---|---|---|
| | Example 4 | Example 5 | Example 6 | Control A |
| | DADE 24 g | DADE 45 g | DADE 56 g | DADE 61 g |
| Tensile Properties[b] | | | | |
| Tensile Strength (ksi) | 13.0 | 13.5 | 15.1 | 10.5 |
| Tensile Modulus (ksi) | 482 | 490 | 465 | 404 |
| Elongation (%) | 3.8 | 4.4 | 3.4 | 3.8 |
| Tg (°C.) Dry | 175 | 180 | 198 | 210 |
| Wet[b] | 130 | 135 | — | 173 |
| Water Uptake (%)[c] | 3.0 | 3.0 | — | 3.4 |

[a]NH/epoxide stoichiometry = 1.0/1.0
[b]ASTM D-638
[c]Measured after soaking in water for two weeks at 71.1° C. (160° F.).

It is apparent that compositions according to the invention have superior tensile strength, tensile modulus, and water resistance compared to Control A.

EXAMPLE 7

This example describes the preparation of an unreinforced casting of BAPTG, MY-720, and 4,4-diaminodiphenylsulfone (DDS).

75 g of the epoxy of Example 1 and 75 g of MY-720 were heated to 100° C. in a 3-neck roundbottom flask equipped with a paddle stirrer, and a thermometer connected to a Therm-o-watch temperature controller. 33 g of DDS were slowly added with stirring. After the mixture had been heated for 90 minutes at 100° C., the diamine had dissolved. The resin was then degassed and poured into a mold (8"×10"×⅛"). The casting was cured in the same manner as Example 4.

TABLE II

| PROPERTIES OF AN UNREINFORCED CASTING | |
|---|---|
| | Example 7[b] |
| Composition | BAPTG 75 g<br>MY-720 75 g<br>DDS 33 g |
| Tensile Properties[a] | |
| Tensile Strength (ksi) | 6.3 |
| Tensile Modulus (ksi) | 672 |
| Elongation (%) | 1.1 |

[a]ASTM D-638
[b]NH/epoxide stoichiometry 0.5/1.0

EXAMPLE 8 and

Control B

This example describes the preparation of unidirectional epoxy/graphite prepreg.

A thermosetting composition like that of Example 4 was prepared by blending 1219 g of BAP TG (EEW=176) and 510 g of the diamine DADE at 100° C. for approximately 90 minutes. At this point, a 1.5 mil film was cast and was determined to have appropriate tack for prepreg. It was coated on 13.5 inch wide release paper (type 2-60-SF-157 and 168A, obtained from Daubert Coated Products Dixon, IL) at a coating weight of 110 g/m².

Twelve-inch wide undirectional prepreg tape was made by forming a ribbon of 78 tows of carbon fiber and contacting it between 2 plies of epoxy-coated release paper in a prepreg machine. In the prepreg machine, the sandwich of fiber and coated release paper passed over a series of heated rollers to melt the resin into the fibers. The finished tape contained about 64 percent by weight of fiber. Its thickness was about 0.007 inches. The fiber was a polyacrylonitrile-based fiber with a tensile strength of $5.5 \times 10^5$ psi and a tensile modulus of $35 \times 10^6$ psi.

Control B

This example is comparative and describes the preparation of unidirectional epoxy/graphite prepreg.

A thermosetting composition like that of Control A was prepared by blending 1227 g of MY-720 and 773 g of DADE. The resin was advanced by heating for 100 minutes at 100° C. After the mixture cooled to 70° C., it was coated on 13.5 inch wide release paper (type 2-60-SF-157 and 168A, obtained from Daubert Coated Products Dixon, IL) at a coating weight of 104 g/m².

Twelve-inch wide undirectional prepreg tape was made by forming a ribbon of 78 tows of carbon fiber and contacting it between 2 plies of epoxy-coated release paper in a prepreg machine. In the prepreg machine, the sandwich of fiber and coated release paper passed over a series of heated rollers to melt the resin into the fibers. The finished tape contained about 70 percent by weight of fiber. Its thickness was about 0.007 inches. The fiber was a polyacrylonitrile-based fiber with a tensile strength of $5.5 \times 10^5$ psi and a tensile modulus of $35 \times 10^6$ psi.

EXAMPLE 9

Example 9 describes the cured unidirectional laminate made from the prepreg of Example 8. The laminate was cured in an autoclave at 355° F. for 2 hours under a pressure of 90 psi. Seven plies of prepreg were used to make the specimen. Compressive properties were measured using a modified ASTM-D695 procedure. Unidirectional graphite/epoxy tabs were added to prevent the sample ends from crushing. A gauge length of approximately 0.188 inches was used. End tabs on compressive samples were adhered using FM-300 film adhesive (obtained from American Cyanamid Company, Havre de Grace, MD), which was cured at 177° C. for 1 hour. The longitudinal compressive strengths of unidirectional laminates of Example 9 is shown in Table III.

TABLE III

| LONGITUDINAL COMPRESSIVE STRENGTH (ksi) CONDITION: | | |
|---|---|---|
| ROOM TEMPERATURE (DRY) | 180° F. (DRY) | 180° F. (WET)[a] |
| 231 | 226 | 195 |

[a]Specimens were soaked in water 2 weeks at 160° F. prior to testing.

For many applications, a longitudinal compressive strength of at least 150 ksi is required. The results in Table III indicate that the compositions of this invention possess excellent compressive strengths even under hot/wet conditions.

EXAMPLE 10 and

Control C

This example demonstrates the compressive strength after impact of a quasiisotropic laminate fabricated with the composition of this invention and with a control. The test employed measures the damage tolerance of composites. The latter depends on the choice of matrix resin. Test specimens had dimensions of 6×4×approximately 0.2 inches. The panels were impacted in the center with a Gardner type Impact Tester (Gardner Laboratories, Bethesda, MD) having a ⅝ inch diameter spherical indenter. The impact was normal to the plane of the fibers. When impacted, the laminate was simply supported over a 3 inch by 5 inch cutout in an aluminum plate with a plywood backup. The impacted panel was tested for residual compressive strength in a steel fixture that constrained the edges from out-of-plane buckling. Results are tabulated in Table IV.

TABLE IV

| RESIDUAL COMPRESSIVE STRENGTH (in $10^3$ psi) AFTER IMPACT RESULTS[a] | | |
|---|---|---|
| EXAMPLE: | EXAMPLE 10 | CONTROL C[b] |
| Impact Level: 1500 (In lb/in) | 24.5 | 19.3 |

[a]Cure schedule: 2 hours at 355° F. Layup: $[+45/90/-45/0]_{3s}$
Autoclave pressure 90 psi
[b]Made from the MY-720/DADE prepreg of Control B It is clear that the residual compressive strength of laminates made with the composition of this invention is significantly higher than that of the control. Thus, the fiber reinforced composites of this invention have improved impact resistance.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:
1. A prepreg, comprising:
   an epoxy resin system comprising a tetraglycidate of the formula

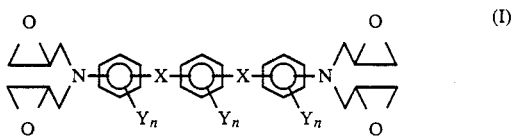

wherein

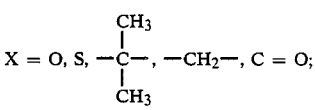

Y=halogen, $C_1$-$C_4$ alkyl; and
n=0 to 4
a polyamine curing agent; and
a fiber reinforcement.

2. A prepreg as defined in claim 1, wherein said polyamine is selected from the group consisting of aliphatic polyamines and polyamines containing benzenoid unsaturation.

3. A prepreg as defined in claim 2, wherein said aliphatic polyamine is selected from the group consisting of diethylene triamine, triethylene tetraamine, and tetraethylene pentaamine 4. A prepreg as defined in claim 2, wherein said polyamine containing benzenoid unsaturation is selected from the group consisting of m-phenylenediamine, p-phenylenediamine, 1,6-diaminonaphthalene, 4,4'-diaminodiphenyl methane, 4,4'-diaminodiphenyl ether, sulfanilamide, 3-methyl-4-aminobenzamide, 4,4'-diaminodiphenyl sulfone, 4,4'-diaminodiphenyl, and ring alkylated derivatives of m-phenylene diamine.

5. A prepreg as defined in claim 1, wherein said polyamine has the formula

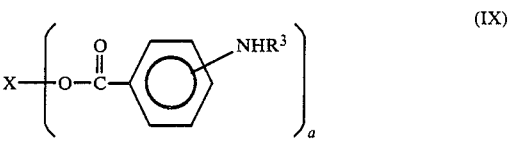

wherein:
a is 2 or 3;
$R^3$ is hydrogen, alkyl of 1 to 8 carbon atoms, or aryl, of 6 to 18 carbon atoms; and X is a divalent or trivalent organic hydrocarbon, hetero-interrupted hydrocarbon, substituted hydrocarbon radical, or

6. A prepreg as defined in claim 5,
wherein
$R^3$ is hydrogen, alkyl of 1 to 3 carbon atoms, or phenyl; and
X is a divalent or trivalent radical selected from
(1) divalent groups consisting of —$(CH_2)_4$— wherein y is an integer of from 2 to 12,

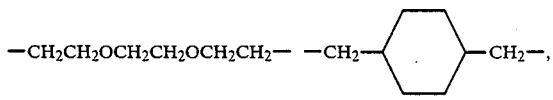

-continued

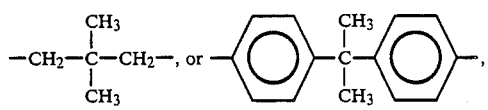 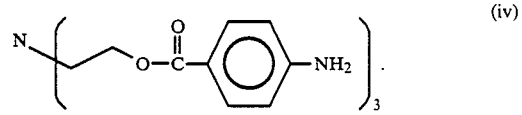

(2) trivalent groups of the formula

and

—(CH$_2$)$_n$—CH—(CH$_2$)$_m$— wherein n and m are the same or different integers from 1 to 4.

7. A prepreg as defined in claim 1, wherein said polyamine is selected from the group consisting of (i) 4,4'-diaminodiphenyl sulfone, (ii) diamines having the formula

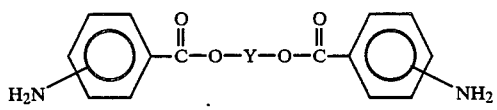

wherein each of the two amino groups is meta or para to the carbonyl group bonded to the same ring and wherein Y is

wherein q is a integer from 2 to 12,

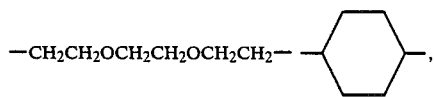

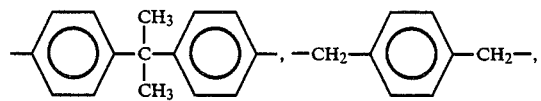

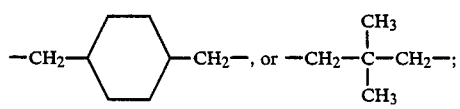, or 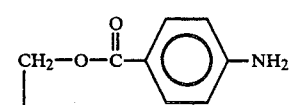;

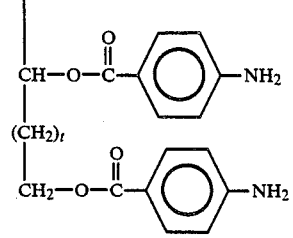

(iii)

wherein t is an integer of from 0 to about 5, and

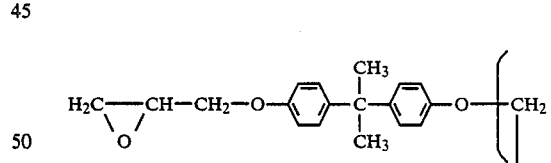

(iv)

8. A prepreg as defined in claim 7, wherein q is from about 2 to about 6.

9. A prepreg as defined in claim 8 wherein q is 3.

10. A prepreg as defined in claim 1, wherein said polyamine curing agent is mixed with said tetraglycidate in an amount which provides about 0.3 to about 2.0 moles of amine hydrogen for each mole of epoxy groups.

11. A prepreg as defined in claim 10, wherein said amount provides about 0.4 to about 1.7 moles of amine hydrogen for each mole of epoxy groups.

12. A prepeg as defined in claim 11, wherein said amount provides about 0.45 to about 1.3 moles of amine hydrogen for each mole of epoxy groups.

13. A prepreg as defined in claim 1, wherein said fiber reinforcement is a material selected from the group consisting of glass, carbon, graphite, silicon carbide, boron, alumina, titania, poly(benzothiazole), poly(benzimidazole), poly(benzoxazole), and aromatic polyamide fibers.

14. A prepreg as defined in claim 1, wherein said fiber reinforcement is in the form of continuous tows, woven cloth, whiskers, chopped fiber, or random mat.

15. A prepreg as defined in claim 1, wherein said epoxy resin system further comprises a co-epoxide.

16. A prepreg as defined in claim 15, wherein said co-epoxide is present in an amount up to about 40 wt. percent based on the total amount of tetraglycidate.

17. A prepreg as defined in claim 16, wherein said co-epoxide is present in an amount up to about 30 wt. percent based on the total amount of tetraglycidate.

18. A prepreg as defined in claim 15, wherein said co-epoxide has the structure

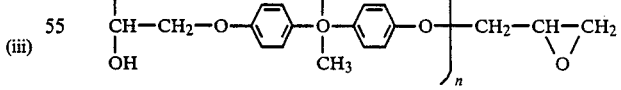

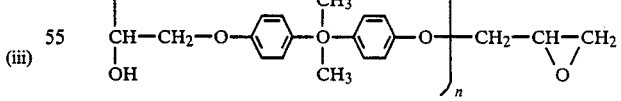

where n has a value from about 0 to about 15.

19. A prepreg as defined in claim 18, wherein n has a value from about 0 to about 10.

20. A prepreg as defined in claim 15, wherein said co-epoxide is a polyepoxide which is a polyglycidyl ether.

21. An epoxy resin system as defined in claim 20, wherein said co-epoxide is a polyepoxide selected from the group consisting of polyglycidyl ethers of 4,4'-dihydroxydiphenyl methane, 4,4'-dihydroxydiphenyl sulfone, 4,4'-biphenol, 4,4'-dihydroxydiphenyl sulfide, phenolphthalein, resorcinol, 4,2'-biphenol, and tris(4-hydroxyphenyl)methane.

22. A prepreg as defined in claim 15, wherein said co-epoxide is a polyglycidyl derivative of a phenol-formaldehyde novolak or a cresol-formaldehyde novolak.

23. A prepreg as defined in claim 22, wherein said phenol-formaldehyde novolak has the structure XI and said cresol-formaldehyde novolak has the structure XII

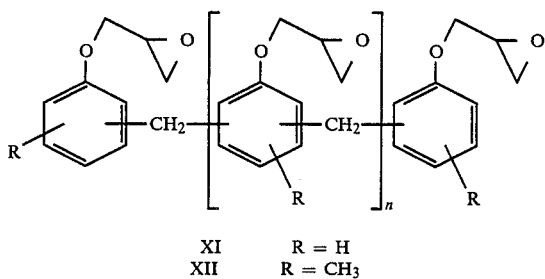

XI  R = H
XII R = CH$_3$ where n=0.1 to 8.

24. A prepreg as defined in claim 15, wherein said co-epoxide is a polyglycidyl adduct of an amine, an aminoalcohol, or a polycarboxylic acid.

25. A prepreg as defined in claim 24, wherein said polyglycidyl adduct of an amine is selected from the group consisting of N,N-diglycidyl aniline, N,N-diglycidyl toluidine, N,N,N',N'-tetraglycidylxylylene diamine, N,N,N',N'-tetraglycidyl-bis(methylamino)cyclohexane, N,N,N',N'-tetraglycidyl-4,4'-methylene dianiline, N,N,N',N'-tetraglycidyl-3,3'-diaminodiphenyl sulfone, and N,N'-dimethyl-N,N'-diglycidyl-4,4'-diaminodiphenyl methane.

26. A prepreg as defined in claim 24, wherein said polyglycidyl adduct of an aminoalcohol is O,N,N,-triglycidyl-3-aminophenol or O,N,N-triglycidyl-4-aminophenol.

27. A prepreg as defined in claim 24, wherein said polyglycidyl adduct of a polycarboxylic acid is a glycidyl ester.

28. A prepreg as defined in claim 27, wherein said glycidyl ester is selected from the group consisting of diglycidyl phthalate, diglycidyl terephthalate, diglycidyl isophthalate, and diglycidyl adipate.

29. A prepreg as defined in claim 15, wherein said co-epoxide is selected from the group consisting of triglycidyl cyanurates and isocyanurates, N,N-diglycidyl oxamides, N,N'-diglycidyl derivatives of hydantoins, diglycidyl esters of cycloaliphatic dicarboxylic acids, and polyglycidyl thioethers of polythiols.

30. A prepreg as defined in claim 15, wherein said co-epoxide is a copolymer of an acrylic acid ester of glycidol with one or more copolymerizable vinyl compounds.

31. A prepreg as defined in claim 15, wherein said co-epoxide is a silicone resin containing epoxy functionality.

32. A prepreg as defined in claim 15, wherein said co-epoxide is an epoxy resin prepared by epoxidation of dienes or polyenes.

33. A prepreg as defined in claim 15, wherein said co-epoxide is cycloaliphatic.

34. A prepreg as defined in claim 1, further comprising a thermoplastic polymer, polymer blend, or elastomer.

* * * * *